United States Patent [19]

Hewitt

[11] Patent Number: 4,967,756
[45] Date of Patent: Nov. 6, 1990

[54] BLOOD PRESSURE AND HEART RATE MONITORING METHOD AND APPARATUS

[75] Inventor: Terry L. Hewitt, Portland, Oreg.

[73] Assignee: Instromedix, Inc., Hillsboro, Oreg.

[21] Appl. No.: 207,313

[22] Filed: Jun. 15, 1988

[51] Int. Cl.5 .............................................. A61B 5/02
[52] U.S. Cl. ..................................... 128/680; 128/708
[58] Field of Search ....................... 128/672, 677–686, 128/904, 708

[56] References Cited

U.S. PATENT DOCUMENTS

| | | | |
|---|---|---|---|
| 4,216,779 | 8/1980 | Squires et al. | 128/708 X |
| 4,252,127 | 2/1981 | Gemelke | 128/680 |
| 4,273,136 | 6/1981 | Kubo et al. | 128/680 |
| 4,313,445 | 2/1982 | Georgi | 128/682 X |
| 4,326,536 | 4/1982 | Kitigawa et al. | 128/682 |
| 4,407,297 | 10/1983 | Croslin | 128/681 |
| 4,461,266 | 7/1984 | Hood, Jr. et al. | 128/680 X |
| 4,501,281 | 2/1985 | Furukawa | 128/680 |
| 4,660,567 | 4/1987 | Kaneko et al. | 128/682 |
| 4,712,564 | 12/1987 | Yamaguchi | 128/682 |
| 4,722,349 | 2/1988 | Baumberg | 128/681 |

Primary Examiner—Max Hindenberg
Attorney, Agent, or Firm—Kolisch, Hartwell & Dickinson

[57] ABSTRACT

Improved ambulatory blood pressure and heart rate monitoring and recording apparatus and method are described. The apparatus uses an auscultatory transducer connected to a microprocessor-based circuit for sensing, validating and recording systolic and diastolic pressure in the cuff-surrounded limb of the patient, and for measuring heart rate. The improved method calculates, and records in the same blood pressure and heart rate data record, an alphanumeric figure of merit, or alternatively a numeric quality index, based upon Korotkoff sound frequency and amplitude criteria. In another improved method, the maximum pressure to which the cuff is pressurized for each measurement is made to track the individual patient's systolic blood pressure to ensure reliable blood pressure readings without unneccessary constriction of the patient's limb.

12 Claims, 6 Drawing Sheets

BLOOD PRESSURE AND HEART RATE MONITORING METHOD AND APPARATUS

BACKGROUND AND SUMMARY OF THE INVENTION

This invention relates generally to auscultatory blood pressure and pulse monitoring method and apparatus. More specifically, it concerns an ambulatory device for the automatic or demand recording and trans-telephonic communication, for later diagnosis, of information including blood pressure, heart rate, time of day, event code and figure of merit. The improved method includes systolic blood pressure-adaptive cuff pressurization and figure of merit computation to ensure that information comfortably, reliably and accurately is monitored and reported.

Typically, ambulatory blood pressure monitoring and recording equipment continuously measures a patient's systolic and diastolic blood pressure for a given period of time. Recent advances in monitoring equipment include the ability of the patient trans-telephonically to communicate information regarding blood pressure to a remote site for permanent storage and either simultaneous or later diagnosis, rather than requiring the patient to return the equipment or a magnetic tape cassette to the physician after each recording session. A serious shortcoming of state-of-the-art equipment is the fact that the pressure cuff which locates the microphone used to pick up auscultatory signals indicative of blood pressure may be less than optimally positioned on the patient's arm, resulting in inadequate signal strength and incomplete or misleading blood pressure data.

Frequently, it is desirable to record blood pressure on demand by the patient, based upon predetermined, physician-selected criteria, e g. upon awakening, while eating or after exercising, rather than continuously or at given times of day that may bear no relation to the individual patient's activity or idiosyncratic behavior. Further, it is desirable continuously to alter the maximum (occlusive) cuff pressure to adapt to the ambulatory patient's level of activity, thereby to ensure that blood flow in the limb is fully occluded but to ensure that the patient's limb is not unnecessarily, and often uncomfortably or even painfully, constricted. Finally, it is desirable to monitor and report to the prescribing physician not only blood pressure and heart rate data, but also information indicative of the quality of, or the figure of merit that may be accorded, such data.

It is a primary object of this invention to provide an ambulatory blood pressure monitoring and recording device capable of indicating to a prescribing physician the quality, or figure of merit, of a contemporaneous or historic blood pressure measurement.

Another object of the invention is to provide such a device that is individual patient physiology- and activity-adaptive, wherein the maximum cuff pressure tracks the rise and fall of the patient's systolic blood pressure, thereby to provide only marginally higher pressure than the amount needed to occlude blood flow in the limb around which the cuff is placed.

These and other objects of the invention will be understood in reference to the following detailed description of the preferred embodiment of the invention, and by reference to the accompanying drawings.

DETAILED DESCRIPTION OF THE PREFERRED EMBODIMENT

Figure 1:
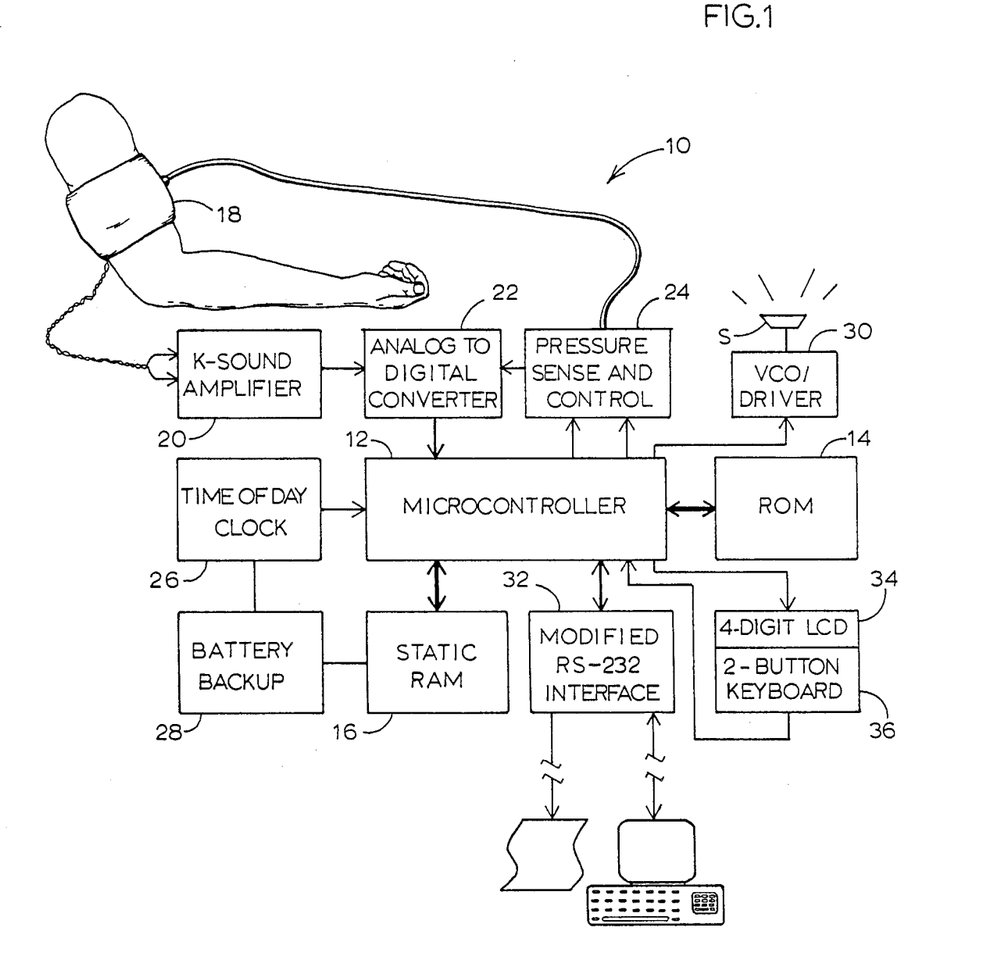
FIG. 1 is a simplified, schematic block diagram of the apparatus of the invention, made in accordance with its preferred embodiment.

Referring first to FIG. 1, a simplified, schematic block diagram of the apparatus of the present invention, indicated generally at 10, is illustrative of its preferred embodiment. In the interest of brevity and clarity, detail intentionally is omitted from FIG. 1, e g. latches, drivers and other detailed, device-level circuitry are not shown It will be understood by those skilled in the art that, depending upon the particular devices chosen to perform the required functions, such circuitry also may be required.

Apparatus 10 is a lightweight, ambulatory, battery-powered device that is capable of measuring, recording and transmitting blood pressure and heart rate data, as well as supplemental information found to have particular utility to a prescribing physician It is self-contained, requiring neither external power nor pump, and conveniently may be carried upon the person of the patient A blood pressure and heart rate reading takes approximately one minute, during which cycle the patient's systolic and diastolic blood pressure are measured by inflating the cuff to a programmed maximum pressure and monitoring the pressure and K-sound inputs as the cuff slowly and steadily deflates In the preferred embodiment of the invention, apparatus 10 is capable of recording at programmed intervals between ten and ninety minutes or on demand for a period of twenty-four hours. As will be seen, apparatus 10 provides the patient with the ability trans-telephonically to transmit data over standard phone lines, thus obviating a visit to the physician each time a recording session is complete.

Apparatus 10 includes computer means, or a microprocessor or microcontroller 12; program storage means, or a read-only memory (ROM) 14; and data storage or recording means, or a read and write memory (RAM) 16. In a manner that will be described below in reference to FIG. 2, a program that is stored in ROM 14 is executed in microcontroller 12 upon application of power via a power switch (not shown), and RAM 16 thereafter is used to store blocks of data pertaining to the patient's blood pressure, heart rate, etc.

Korotkoff sounds (K-sounds) and static (DC) and dynamic (AC) blood pressure data are acquired and are discriminated from noise and other artifacts (particularly motion artifacts), as by any of a variety of known means and methods that form no part of the present invention. The K-sounds are sensed by a microphone (not shown) which is taped on the patient's arm underneath a pressurizable cuff 18 that surrounds the arm. In the auscultatory method, K-sounds are detected acoustically to produce a signal representative thereof. In the preferred embodiment of the invention, K-sound detecting means include the microphone and its signal conditioner, K-sound amplifier 20, the output of which may be selected as an output from a multiplexer (not shown) associated with an analog to digital converter (ADC) 22, which produces an eight-bit digital value approximately once every 100 microseconds. This byte then is inputted to microcontroller 12 via one of its data ports. Cuff 18 is pressurized, and static pressure (the slowly, steadily declining cuff pressure) and dynamic pressure (the pulse waveform blood pressure) are monitored by pressure sense and control circuit 24, which includes a pressure transducer, a pump and a cutoff valve, all of which are integral to the housing (not shown) in which the diagrammed circuitry is enclosed Static and dynamic pressure readings are provided in eight-bit digital format to microcontroller 12 via the multiplexer associated with ADC 22.

Referring still to FIG. 1, the remaining parts of the block diagram of apparatus 10 now briefly will be described. A programmable time of day clock 26 provides means for recording, with the blood pressure and heart rate data, the time of day at which, and the date on which, the reading was taken. As they must retain their otherwise volatile memories in the event of battery discharge or failure, RAM 16 and clock 26 are powered by a battery backup circuit 28. Trans-telephonic means for communicating blood pressure and other data to a remote site for diagnosis includes a voltage controlled oscillator (VCO) and speaker driver circuit 30 enable frequency shift keyed (FSK) tone generation via speaker S, as by a telephone transmitter being placed adjacent a small hole in the enclosure. The tone frequencies used in the preferred embodiment of the invention are nominally 1900 and 2500 Hz. A modified RS-232 serial interface 32 is provided for data communication from apparatus 10 to a parallel printer (shown schematically to the left in FIG. 1) or to and from data terminal equipment (DTE), e.g. a computer (shown schematically to the right in FIG. 1), which complies with the RS-232 telecommunications standard. Finally, a four-digit, seven-segment liquid crystal display (LCD) 34 and a two-pushbutton (four-position) keyboard 36 enable the physician, the patient or the service technician to view certain parameters stored in ROM 14 or RAM 16 and, if desired, to change them.

Turning now to FIG. 2, a flowchart of the FIGURE OF MERIT software routine implemented according to the preferred method of the invention, is shown It will be appreciated that diagramming conventions have been adopted, including a generally top-to-bottom and left-to-right directional flow. The ellipses indicate entry points to routines or subroutines, exit points from routines or subroutines, or off-sheet connectors to other parts of FIGS. 2A through 2E, which span five sheets (e.g. entry/exit points/off-sheet connectors designated 100, 102, 104, 106, 108, 110, 112, 114, 116, 118, 120). The rectangles indicate task or action blocks (e.g. actions blocks designated 122, 124, 126, 128, 130, 132, 134, 136, 138, 140, 142, 144, 146, 148, 150, 152, 154, 156, 158, 160, 162, 164, 166, 168, 170, 172, 174). The rhombuses indicate decision blocks (e.g. decision blocks 176, 178, 180, 182, 184, 186, 188, 190, 192, 194, 196, 198, 200, 202, 204, 206, 208, 210, 212, 214, 216, 218, 220, 222, 224, 226, 228), with the answer to the enclosed question determining the decisional path next to be taken. The flowcharts of FIGS. 2A through 2E are quite self-explanatory to those of ordinary skill in computer science and allied arts, and will not, therefore, be discussed in detail. It is noted that, unless otherwise indicated in the specification, numeric values are decimal and alphanumerics within quotes, e.g. "A1", are American Standard Code for Information Interchange (ASCII) characters.

Figure 2A:
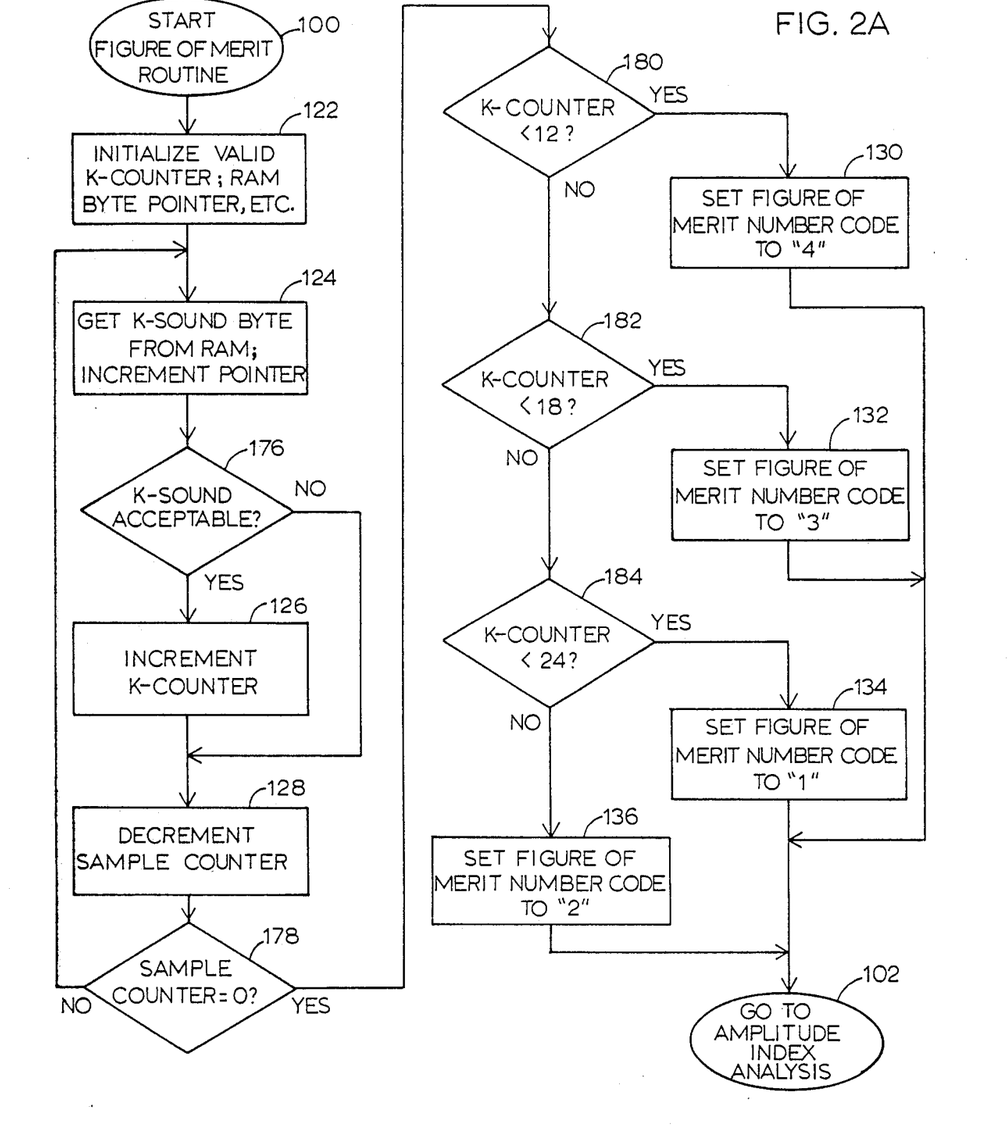
FIG. 2A-2E is a flowchart of the figure of merit software routine as it is implemented in accordance with the preferred method of the invention.

Referring first to FIG. 2A, which contains the entry point to the FIGURE OF MERIT routine, it is noted that K-COUNTER is a variable that represents the number of acceptable K-SOUNDs that are encountered. (K-sound acceptability may be based upon any of a wide range of known criteria including, for example, an acceptably low rate of change in the indicated heart rate, as may be derived from AC pressure, as well as corresponding K-sound, waveform timing.) It is initialized to zero. Upon entry to the FIGURE OF MERIT routine, the variable SAMPLE COUNTER contains the number of K-SOUNDs that have been sampled over the sampling interval (which may be a test interval which number or count is referred to herein as K-sound frequency or a more normal, automatic or demand recording session or event). Finally, upon entry to the routine, variable RAM BYTE POINTER contains the address of the first of consecutive bytes in RAM 16 which contain K-SOUND amplitude values. Thus, RAM BYTE POINTER is used as a pointer into the RAM buffer segment of memory.

The software flowcharted in FIG. 2A counts the number of acceptable K-SOUND samples over the interval and assigns a NUMBER CODE between 1 and 4 (inclusive), depending upon whether K-COUNTER is less than twelve; greater than or equal to twelve but less than eighteen; greater than or equal to eighteen but less than twenty-four; or greater than or equal to twenty-four The NUMBER CODEs assigned for each of the above categories are, respectively, "4"; "3"; "2"; and "1." Once a NUMBER CODE is assigned based upon K-sound frequency, control is transferred to an AMPLITUDE INDEX ANALYSIS routine.

Figure 2B:
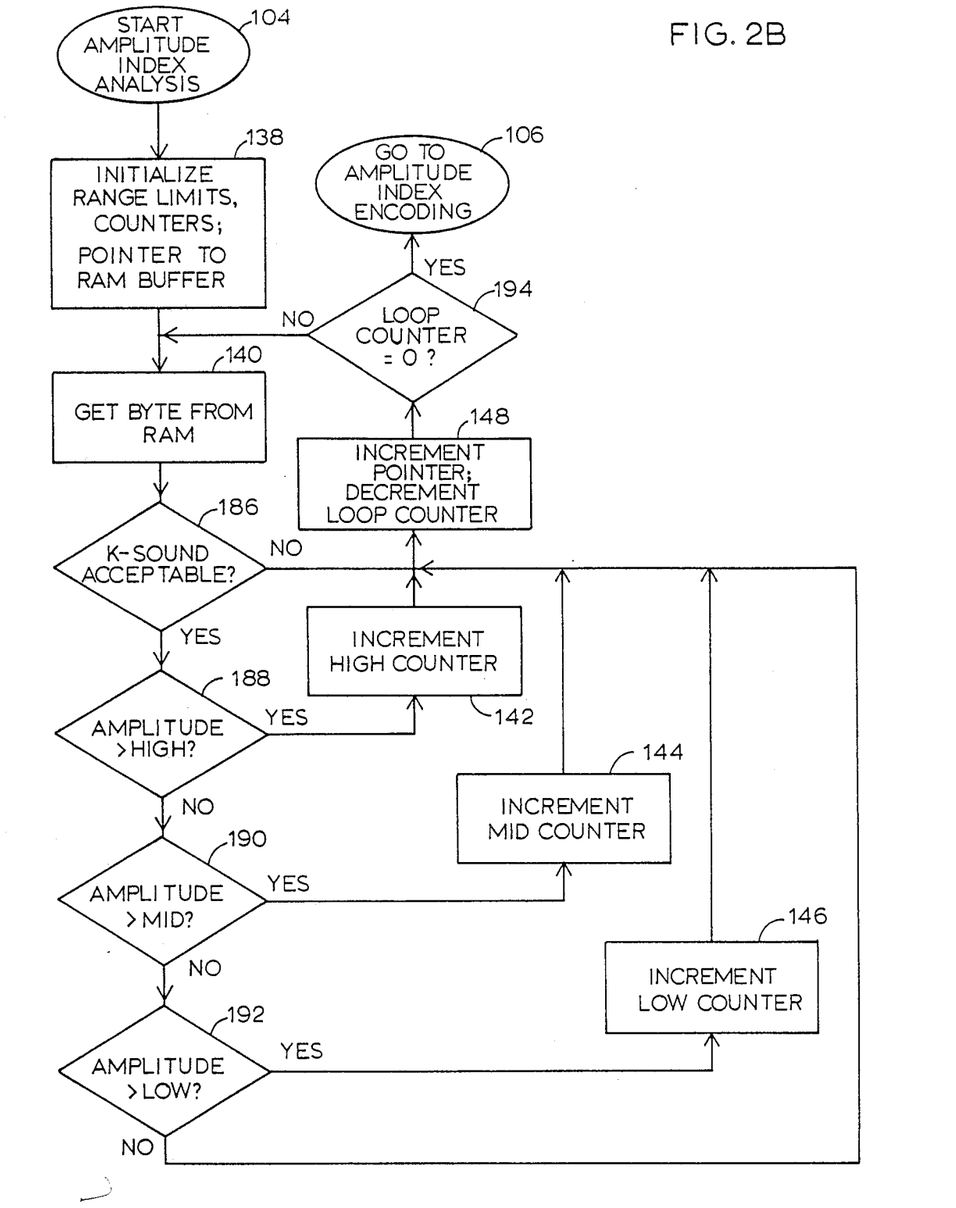
Figure 2C:
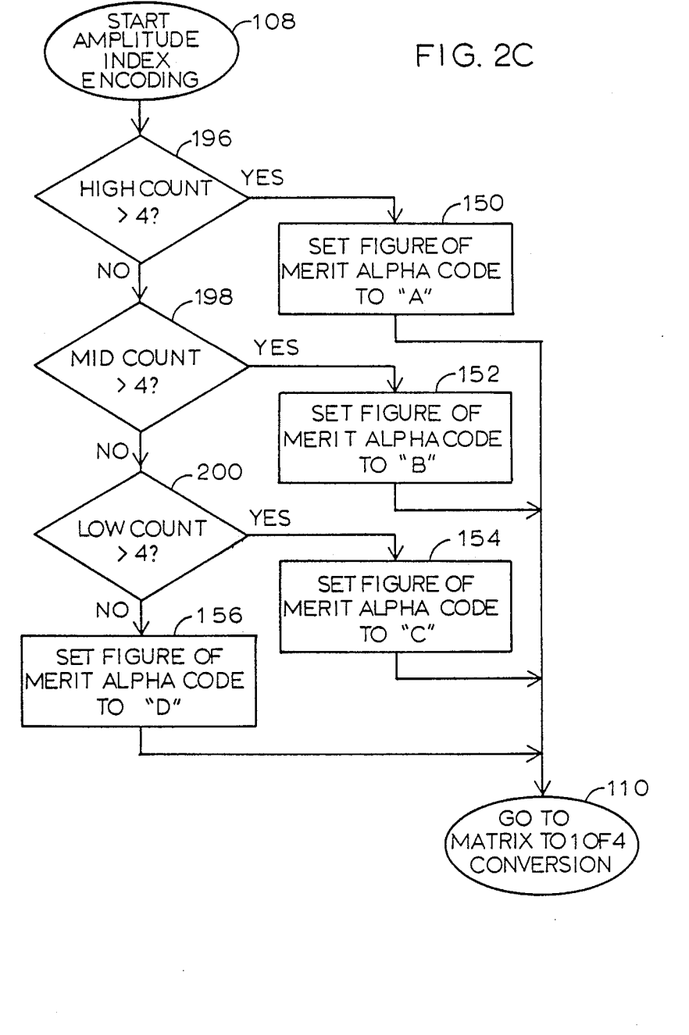

FIGS. 2B and 2C flowchart the software routine that analyzes the peak amplitudes of the K-sounds, categorizes them as falling within one of four K-sound ranges and encodes them into a corresponding one of four, symbolic ALPHA CODEs. These ALPHA CODEs, when considered in light of the distinctive, symbolic NUMBER CODEs assigned in the routine described immediately above, have been found to give valuable information to the physician regarding the quality, or figure of merit, of the data which was simultaneously recorded therewith.

The software flowcharted in FIG. 2B initializes three range limit variables, HIGH, MID and LOW, to the preferred values 192, 128 and 64, respectively (the maximum value of the output of eight-bit ADC 22 is 255, which may be made to represent the maximum K-sound amplitude of interest by conventional null and gain adjustment of amplifier 20 and ADC 22); initializes a variable POINTER to the address of the RAM buffer; initializes a variable LOOP COUNTER to the number of K-sound samples to be analyzed and clears three variables, HIGH COUNTER, MID COUNTER and LOW COUNTER. Peak amplitude values representing acceptable K-sounds are compared with these variables and HIGH COUNTER, MID COUNTER and LOW COUNTER selectively are incremented to indicate the frequencies with which the sampled peak amplitudes are within the three ranges. When LOOP COUNTER is decremented to zero (when the samples are exhausted), control is passed to the AMPLITUDE INDEX ENCODING routine.

FIG. 2C illustrates the process by which the results of the amplitude index analysis are encoded into the ALPHA CODE alluded to above Each of the HIGH, MID and LOW COUNTERs are compared to a predetermined value which, in the preferred method of the invention, is 4. If more than four HIGH amplitude K- sounds were counted, then the variable ALPHA CODE is set to "A." If more than four MID amplitude K-sounds were counted, then ALPHA CODE is set to "B." If more than four LOW amplitude K-sounds were counted, then ALPHA CODE is set to "C." If none of the above is true, then ALPHA CODE is set to "D." The two-digit, alphanumeric code which is formed by concatenating a NUMBER CODE and an ALPHA CODE representing, respectively, the frequency and amplitude of the K-sounds, is referred to herein as a figure of merit. It may be thought of as representing a two-dimensional matrix in which, for example, a blood pressure measurement having associated with it a figure of merit of "A1" would earn a high confidence rating, whereas a blood pressure measurement having associated with it a figure of merit of D4 would be suspect. Preferably, the alphanumeric code generated by the routine is stored in a data record, within RAM 16, for example, containing the blood pressure and heart rate data recorded during the (demand) event or (automatic) session, thereby to associate a figure of merit with the blood pressure data the quality of which it characterizes.

Operatively coupling the software illustrated in FIG. 2 with computer means provides means integral with more conventional blood pressure monitoring and recording apparatus for qualitatively characterizing such blood pressure data. This characterizing means includes software means for evaluating the data, based upon predetermined criteria e.g. based upon the frequency and amplitude of the accompanying K-sounds. The result of such evaluation is quality indicia, such as the figure of merit or the quality index produced by the illustrated software which executes in microcontroller 12. Finally, in the illustrated embodiment, these quality indicia are encoded, by the software flowcharted in FIGS. 2C through 2E, to produce symbolic data interpretable as representing the K-sound-based figure of merit or quality index.

It will be appreciated that, by executing the software described above concurrently with conventional K-sound and AC blood pressure sampling and accepting software (e g. the AMPLITUDE INDEX ANALYSIS routine may be defined as a task which is begun whenever the K-sound RAM buffer fills), a highly significant, stored result obtains. It is now possible, during analysis and diagnosis of blood pressure history, to evaluate the 'cold' blood pressure data in the light of objective data recorded simultaneously therewith Such a figure of merit also may be viewed in real time by the patient or physician on LCD 34, thereby giving immediate feedback on the merit of any recorded measurements. If indicated, appropriate corrective action may be taken immediately, e.g one may better locate cuff 18 or its integral microphone, relative to the limb.

In a proposed modification to the preferred method of the invention, the alphanumeric figure of merit is converted to a single one of four numeric digits, referred to herein as a K-sound quality index, by the mapping illustrated in Table 1.

TABLE 1

|   | 1 | 2 | 3 | 4 |
|---|---|---|---|---|
| A | 1 | 1 | 2 | 3 |
| B | 1 | 2 | 2 | 3 |
| C | 2 | 2 | 3 | 4 |
| D | 3 | 3 | 4 | 4 |

It may be seen from Table 1 that a number between one and four has been assigned to each of sixteen matrix positions at the intersection of a NUMBER CODEd column and an ALPHA CODEd row. It will be appreciated that other assignments, or mappings, may be employed within the spirit of the invention. For example, if it is thought that K-sound frequency is a relatively better indicator of the quality of a blood pressure measurement than is K-sound amplitude, the mapping may be biased (weighted), or made to be asymmetric with respect to its top-to-bottom, left-to-right, diagonal axis.

Figure 2D:
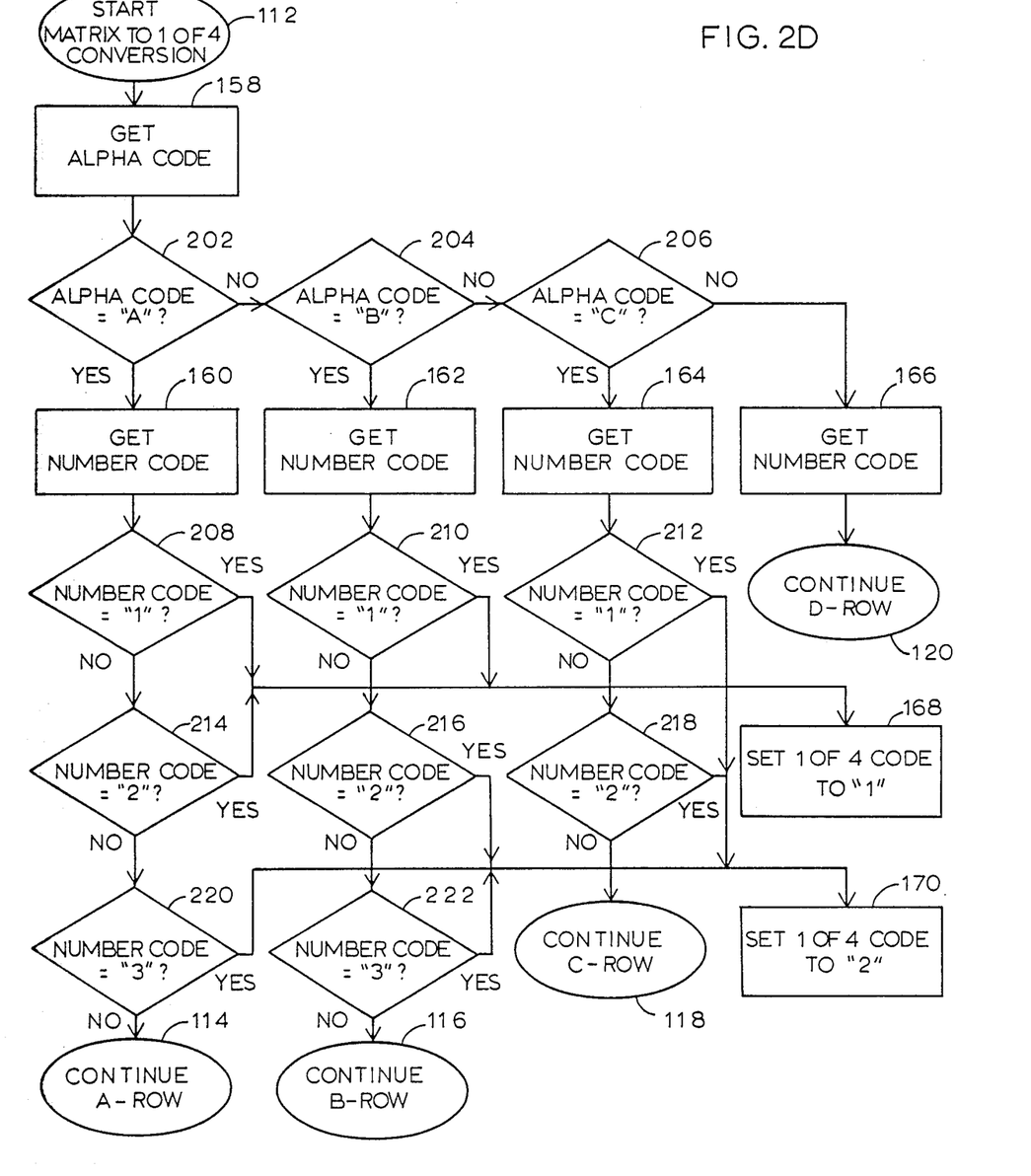
Figure 2E:
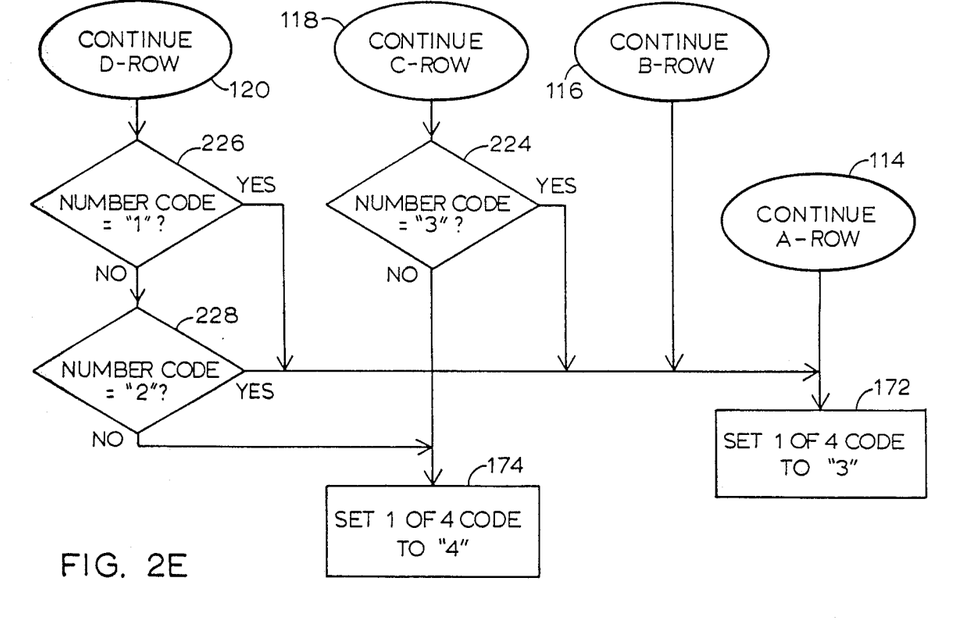

Turning next to FIGS. 2D and 2E, a flowchart illustrating this MATRIX TO 1 OF 4 CONVERSION routine is described It will be appreciated how straightforwardly the mapping illustrated in Table 1 may be performed. It will also be appreciated that the mapping may, within the spirit of the invention, be done in hardware rather than software. The software flowcharted in FIG. 2D first determines which ALPHA CODE is contained in the figure of merit. It then determines, for whichever of the four cases, which NUMBER CODE is contained in the figure of merit. The input paths to the SET 1 OF 4 CODE TO "1" (indicating relatively high quality) action block include any of the following figures of merit "A1", "A2" or "B1. " The input criteria to the SET 1 OF 4 CODE TO "2" action block include "A3", "B2", "B3", "C1" or "C2. " If none of these figures of merit is present in the figure of merit buffer segment of RAM 16, then control is transferred to the appropriate continuation ROW. In FIG. 2E, it may be seen that "A4", "B4", "C3", "D1" or "D2" figures of merit result in the setting of the 1 OF 4 CODE to "3." Finally, "C4", "D3" or "D4" as a figure of merit maps into a "4" K-sound quality index (indicating relatively low quality).

It is important that cuff 18 be pressurized to a level above that of the patient's systolic blood pressure. In the preferred embodiment of the present invention, cuff 18 is pressurized to a default (maximum) value, stored as variable MAXP, under the control of microcontroller 12, and systolic blood pressure readings then are taken. If the measured systolic blood pressure value, stored as variable SYS, is within a predetermined range of, or exceeds, the default value MAXP (determined, for example, by too early a systolic blood pressure, or C, peak in the pressure pulse waveform), then the default value is increased by a predetermined amount. The improved method thus ensures that reliable readings are taken of the patient's systolic blood pressure, e.g that cuff 18 is pressurized sufficiently to occlude the flow of blood in the patient's arm.

It is possible, but not desirable, to overinflate a blood pressure cuff This is especially a risk with prior art blood pressure monitoring equipment having automatic, cuff pressurizing pumps As there is no trained physician manually inflating the cuff and determining when arterial occlusion has occurred, there is a risk of discomfort, or worse, pain or injury, in using automatic blood pressure monitoring equipment. Conventional, ambulatory blood pressure monitoring equipment is capable only of establishing a maximum cuff pressure based upon physiological norms, i.e. a pressure is established that is believed to be sufficient to occlude blood flow, but insufficient to cause discomfort.

Conventional ambulatory blood pressure monitoring equipment fails to accommodate differences among individual patients. The fact is, different patients require different occlusion pressures. Further, an individual's systolic pressure fluctuates widely over time. For example, a person's systolic pressure generally is lower when the person is at rest than when the person is exercising. For this reason, it is believed to be important that the cuff pressurization dynamically track an individual's systolic pressure as it rises and falls throughout the day. The improved method of the present invention accomplishes this dynamic tracking by measuring the systolic blood pressure, comparing it to the cuff pressurization maximum and adding to or subtracting from the maximum a predetermined, incremental value. The novel systolic pressure-adaptive cuff pressurization method of the present invention is especially useful for diagnosis and treatment of patients who are sensitive to cuff tightness.

The novel, systolic pressure-adaptive cuff pressurization feature of the present invention may be better understood by reference to the following pseudo-code listing:

if SYS>MAXP then
    MAXP :=(MAXP+20);
else if MAXP<(SYS+25) then
    if (SYS+15)<MAXP then
        MAXP :=(MAXP+10);
    else MAXP :=(MAXP+20);
else if MAXP>(SYS+45) then
    if MAXP>(SYS+50) then
        MAXP :=(MAXP-10);
    else MAXP :=(MAXP-5);
else no adjustment.

It is believed that the method of adjusting the maximum cuff pressure to accommodate the rise and fall of the patient's systolic pressure may be understood from the pseudo-code. Briefly summarized, the method involves replacement of the default maximum cuff pressure value with a value that is equal to the default value plus or minus an incremental value which has been determined by trial and error to produce the desired response to a wide range of systolic pressure dynamics. By comparing the measured systolic blood pressure with a first predefined maximum pressure and, based upon such comparison, either adding a predefined amount or subtracting a predefined amount from the first predefined maximum to produce a second maximum cuff pressure value, over a period of time including one or more recording sessions in which the MAXP adjustments described above are made, the maximum cuff pressure in successive pressurization and measurement cycles will seek a level that is within a predetermined range above the patient's systolic blood pressure. In this way, the maximum cuff pressure tracks the rise and fall of the patient's systolic blood pressure.

It may be seen from the cuff pressurization method that the desired 'window' for MAXP is 25-45 mm Hg above the patient's systolic blood pressure In the preferred embodiment of the invention, the maximum increment, or upward adjustment, of MAXP is 30 mm Hg above the physician-selected maximum value. Not indicated is that, in the preferred embodiment, MAXP is not permitted to fall below 140 mm Hg. This is to avoid unduly long 'warm-up' periods, during which the cuff pressure is below the systolic blood pressure and blood pressure and heart rate readings are assumed to be inaccurate. Of course, the particular values used or the steps taken to adjust the maximum cuff pressure dynamically to adapt to the patient may differ from the specifics of the preceding discussion, without departing from the spirit of the invention.

The software described in reference to FIG. 2, when operatively coupled with K-sound detecting means described in reference to FIG. 1, provides means for qualitatively characterizing a patient's blood pressure data proximate in time to the monitoring and recording of the blood pressure data. The important advantage of this improvement to ambulatory patient blood pressure monitoring apparatus is that the physician is provided not only with blood pressure data, but also with supplemental information that may be interpreted as more broadly indicative of the context in which the recording was made. For example, when the Figure of Merit is analyzed, it may be found that the K-sound frequency was too low to accord any weight to the blood pressure readings taken during the previous twenty-four hour period, and repositioning of the microphone and/or the pressure cuff may be indicated. It may also be discovered that the amplitude of the K-sounds was too low, indicating that an individual patient's physiology requires a more sensitive, and perhaps an invasive, diagnostic monitoring technique. Finally, particular readings may be determined to be suspect, and may thus be disregarded by the physician, when, despite the general high quality index of most of the readings, one or two are indicated as having been taken during a time when low frequency or low amplitude K-sounds were detected. This might indicate excessive motion on the part of the patient during certain blood pressure readings, for example, rather than an aberrational blood pressure or pulse, which might otherwise indicate a dysfunctional cardiology.

The improved method of ambulatory patient blood pressure monitoring and recording then includes the steps of (1) monitoring patient blood pressure data over a predetermined period of time, (2) monitoring Korotkoff sound amplitude and or frequency for the predetermined period of time, and (3) generating a code which characterizes the blood pressure data based upon an evaluation of the K-sound data. Specifically, generating a code involves assigning one of a first set of plural symbols to represent the Korotkoff sound frequency, assigning one of a second set of symbols distinctive from said first set of symbols to represent the Korotkoff sound amplitudes, and concatenating said one of said first set of symbols with said one of said second set of symbols. In accordance with the preferred method of the invention, one set of symbols is alphabetic and the other is numeric, as in "A1", and D4. As described above, computer means 12 cooperate, in the preferred embodiment of the invention, with pressure sense means, Korotkoff sound detecting means and memory means to monitor the blood pressure and Korotkoff sounds, and to generate the code, which by one method is a two-digit figure of merit, and by another is a single-digit quality index.

By another improved method of the invention, systolic pressure-adaptive means for pressurizing a cuff are capable of adapting to the patient's systolic blood pressure, thereby to ensure that the maximum cuff pressure is within a predetermined pressure range above the patient's systolic blood pressure during such blood pressure data monitoring and recording. Cuff pressure is adjusted by elevating the cuff pressure (which may be thought of as counter-pressure) to a predetermined maximum value, measuring the patient's systolic blood pressure as the static cuff pressure declines, and comparing the measured systolic pressure with the maximum pressure value. An adjustment then is made to the maximum pressure value (variable MAXP in memory), based upon the comparison result, which adds to or subtracts from that value an amount calculated to maintain the cuff pressure within a predetermined range above the patient's systolic blood pressure.

Accordingly, while a preferred method for practicing the invention, and a preferred embodiment of the apparatus of the invention and a proposed modification thereto have been described herein, it is appreciated that further modifications are possible that come within the scope of the invention.

It is claimed and desired to secure by Letters Patent:

1. Ambulatory patient blood pressure monitoring and recording apparatus comprising:
   means for monitoring and recording a patient's blood pressure over a given interval of time;
   means operatively connected with said monitoring-recording means for qualitatively characterizing such recorded blood pressure, said characterizing means including means for evaluating such blood pressure based upon predetermined criteria including the number of Korotkoff sounds detected over said given interval of time to produce quality indicia regarding the merit of such recorded blood pressure, said characterizing means further including means for encoding such quality indicia to produce symbolic data interpretable as being representative of such quality indicia.

2. The improvement of claim 1, which further comprises means integral with such monitoring apparatus for recording said symbolic data such that it is associable with such blood pressure data that it characterizes.

3. The improvement of claim 2, further comprising means for trans-telephonically communicating such blood pressure data and said symbolic data to a remote site for diagnosis.

4. The improvement of claim 1, in which systolic blood pressure is measured by such apparatus having an integral automatic pump means for elevating the pressure of such cuff to a predefined first maximum value, further comprising systolic blood pressure-adaptive means for changing said predefined first maximum value, responsive to a change in such systolic blood pressure, thereby to ensure that the pressure of such cuff substantially is maintained within a predefined pressure range above such systolic blood pressure.

5. An improved ambulatory patient blood pressure monitoring method, for use with means for detecting the Korotkoff sounds produced by such patient's pulse, comprising:
   monitoring and recording blood pressure data over a given time interval,
   evaluating the number of Korotkoff sounds which meet predetermined criteria over said interval of time to produce indicia of the quality of such blood pressure data; and
   encoding said quality indicia to produce symbolic data which is interpretable as indicative of the quality of such blood pressure data.

6. The method of claim 5, which further comprises evaluating the amplitude of Korotkoff sounds which meet predetermined criteria over said interval of time to produce indicia of the quality of such blood pressure data.

7. The method of claim 6, wherein said encoding includes assigning one of a first set of plural symbols to represent the number of such Korotkoff sounds, assigning one of a second set of symbols distinctive from said first set of symbols to represent the amplitudes of such Korotkoff sounds, and concatenating said one of said first set of symbols with said one of said second set of symbols to produce a plural symbol code indicative of the quality of such blood pressure data.

8. The method of claim 7, which further comprises storing said symbolic code in such manner that it is associable with such recorded blood pressure data.

9. The method of claim 8, which further comprises trans-telephonically communicating such recorded blood pressure data and such stored symbolic code to a remote site for diagnosis.

10. An ambulatory patient blood pressure monitoring method for the long-term monitoring and recording of blood pressure data by successive pressurizations of a cuff surrounding a limb of the patient, comprising:
    elevating the pressure of such cuff to a predefined first maximum value;
    measuring the patient's systolic blood pressure;
    comparing said measured systolic blood pressure with said first maximum value;
    calculating a second maximum value, based upon said first maximum value and the result of said comparing, in such manner that said second maximum value is closer than said first maximum value to a predefined range of pressure values above such systolic blood pressure; and
    substituting said predefined first maximum value by said second maximum value for subsequent pressurization of such cuff; thereby
    establishing and thereafter maintaining the pressure to which the cuff is elevated during successive pressurizations thereof within such predefined range of pressure values above successively measured systolic blood pressures.

11. The method of claim 10, wherein said comparing includes determining when such systolic pressure is greater than said first maximum value, and wherein said calculating is performed by adding a predetermined constant value to said first maximum value to produce said second maximum value.

12. The method of claim 11, wherein said comparing includes determining when such systolic pressure is less than or equal to said first maximum value and determining when the difference between such systolic pressure and said first maximum value is greater than a predetermined amount, and wherein said calculating is performed by subtracting a predefined, constant value from said first maximum value to produce said second maximum value.

* * * * *